United States Patent [19]

Saito et al.

[11] Patent Number: 4,932,999
[45] Date of Patent: Jun. 12, 1990

[54] PYRIMIDINE COMPOUNDS, AND HERBICIDAL METHOD AND COMPOSITIONS

[75] Inventors: Yoshihiro Saito; Nobuhide Wada, both of Kakegawa; Shoji Kusano, Hamamatsu; Takeshige Miyazawa; Satoru Takahashi, both of Shizuoka; Yasuhumi Toyokawa, Tokyo; Ikuo Kajiwara, Nagaokakyo, all of Japan

[73] Assignees: Kumiai Chemical Industry Co., Ltd.; Ihara Chemical Industry Co., Ltd., both of Tokyo, Japan

[21] Appl. No.: 415,871

[22] Filed: Oct. 2, 1989

Related U.S. Application Data

[63] Continuation-in-part of Ser. No. 264,015, Oct. 28, 1988.

[30] Foreign Application Priority Data

Nov. 4, 1987 [JP] Japan .................................. 62-278894

[51] Int. Cl.⁵ .................... A01N 43/54; C07D 239/46
[52] U.S. Cl. ........................................ 71/92; 544/299;
544/302; 544/303; 544/225

[58] Field of Search ............... 544/299, 302, 303, 225; 71/92

[56] References Cited

U.S. PATENT DOCUMENTS 4,427,437  1/1984  Serban et al. ...................... 544/312
4,770,691  9/1988  Nezu et al. ............................. 71/92

Primary Examiner—Cecilia Shen
Attorney, Agent, or Firm—Oblon, Spivak, McClelland, Maier & Neustadt

[57] ABSTRACT

A pyrimidine compound having the formula:

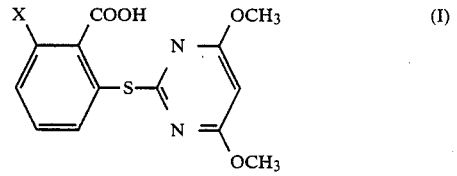

wherein X is a halogen atom, or a salt thereof.

6 Claims, No Drawings

PYRIMIDINE COMPOUNDS, AND HERBICIDAL METHOD AND COMPOSITIONS

This application is a continuation-in-part application of the application Ser. No. 07/264,015 having a filing date of Oct. 28, 1988.

BACKGROUND OF THE INVENTION

1. Field of the Invention

The present invention relates to novel pyrimidine compounds or their salts, herbicidal compositions containing them, and a herbicidal method for applying them.

2. Discussion of Background

Recently, a number of herbicides have been developed and practically used, and they have contributed to the saving of energy for the agricultural operations and to the improvement of the production efficiency. Further, it has been known that various 2-phenoxypyrimidine derivatives are effective as herbicides ((1) U.S. Pat. No. 4,770,691, (2) U.S. Pat. No. 4,427,437 and (3) Agr. Biol. Chem. Vol. 30, No. 9, p. 896 (1966)).

However, the compounds disclosed in the above reference (1) have a problem with respect to the safety to crop plants, although they have exhibited high herbicidal effects. On the other hand, the compounds disclosed in the above references (2) and (3) have drawbacks that their herbicidal activities against annual weeds are inadequate, and they exhibit no substantial activities against perennial weeds.

SUMMARY OF THE INVENTION

The present inventors have conducted extensive research on pyrimidine compounds with an aim to develop a compound having more excellent herbicidal activities, and as a result, have found that the compounds of the present invention having substituents introduced at specific positions of the pyrimidine and benzene rings of phenylthiopyrimidine derivatives, exhibit excellent herbicidal effects against perennial weeds as well as annual weeds, and at the same time, they have a high level of safety to crop platns, particularly to cotton.

The present invention has been accomplished on the basis of these discoveries.

The present invention provides a pyrimidine compound having the formula:

(I)

wherein X is a halogen atom such as chlorine, bromine, iodine or fluorine, preferably bromine or iodine, or a salt thereof.

Further, the salt of the pyrimidine compound of the present invention includes an alkali metal salt, an alkaline earth metal salt, a transition metal salt and an organic ammonium salt.

The present invention also provides a herbicidal composition comprising a herbicidally effective amount of a pyrimidine compound of the formula I or a salt thereof, and an agricultural adjuvant.

Further, the present invention provides a method for killing weeds which comprises applying a herbicidally effective amount of a pyrimidine compound of the formula I or a salt thereof to a locus to be protected.

DETAILED DESCRIPTION OF THE PREFERRED EMBODIMENTS

Now, typical examples of the compound of the present invention will be presented in Table 1. Compound Nos. given in the Table will be referred to in the subsequent description in the specification.

TABLE 1

| No. | R | X | Melting point |
|---|---|---|---|
| 1 | H | Cl | 148~151 |
| 2 | H | F | 133~135 |
| 3 | $H_3NCH(CH_3)CH_3$ | Cl | 149~151 |
| 4 | .HN($C_2H_4OH$)$_3$ | Cl | 94~101 |
| 5 | .Na | Cl | 246~250 |
| 6 | .$H_2N(C_2H_4OH)_2$ | Cl | Not measurable |
| 7 | ⅓Fe | Cl | 140~145 |
| 8 | ½Ca | Cl | 172~175 |
| 9 | .$NH_4$ | Cl | 150~154 |
| 10 | H | Br | 164~165 |
| 11 | H | I | 159~163 |
| 12 | .HN($C_2H_4OH$)$_3$ | Br | 105~111 |
| 13 | .Na | Br | 263~265 |
| 14 | .HN($C_2H_4OH$)$_3$ | I | 82~85 |
| 15 | .Na | I | 262~265 |

The compound of the present invention can be prepared in accordance with the following process.

In the formulas, X is a halogen atom, and $Y^1$ is a halogen atom, an alkylsulfonyl group or a substituted or unsubstituted benzylsulfonyl group.

The compound of the formula I of the present invention can be prepared by reacting the compound of the formula II with the compound of the formula III in the presence of a base, preferably in an inert solvent, at a temperature within a range of from room temperature to the boiling point of the solvent for 1 to 24 hours. When the reaction is conducted without a solvent, the reaction can be conducted by using an alkali metal carbonate as a base, such as anhydrous sodium carbonate at a temperature within a range of from 120 to 160° C.

The solvent used for this reaction includes, for example, a hydrocarbon solvent such as benzene, toluene or xylene, a halogenated hydrocarbon solvent such as methylene chloride or chloroform, an alcohol solvent such as methanol, ethanol, 2-propanol, an ether solvent such as ethyl ether, isopropyl ether, tetrahydrofuran or 1,4-dioxane, a ketone solvent such as acetone or methyl ethyl ketone, an ester solvent such as methyl acetate or ethyl acetate, an aprotic non-polar solvent such as N,N-dimethylformamide, N,N-dimethylacetamide or dimethylsulfoxide, acetonitrile, and water.

As the base, there may be mentioned an alkali metal such as sodium metal or potassium metal, an alkali metal hydride or an alkaline earth metal hydride such as sodium hydride, potassium hydride or calcium hydride, a carbonate such as sodium carbonate, potassium carbonate, sodium hydrogencarbonate or potassium hydrogencarbonate and a metal hydroxide such as sodium hydroxide, potassium hydroxide or calcium hydroxide.

The compound of the formula II which is used in the present invention can be prepared from a known compound anthranilic acid by the known method Sandmeyer reaction.

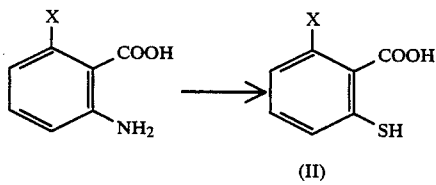

(II)

Or, the compound of the formula II can be prepared from the corresponding salicylic acid derivative by heat rearrangement.

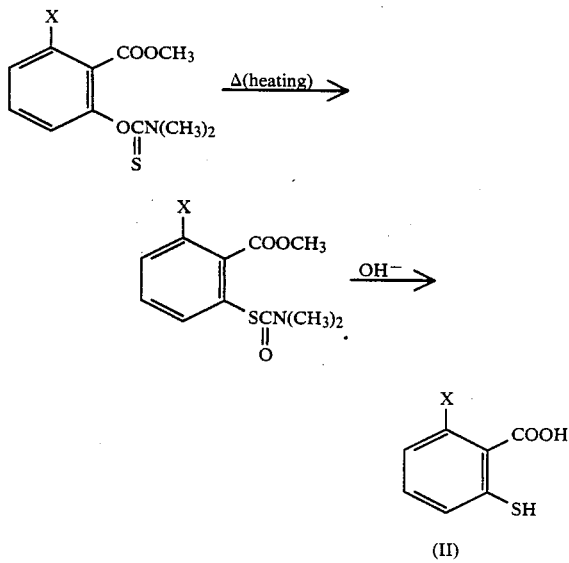

(II)

Or, the compound of the formula II can be prepared from a 2,6-dihalogenobenzonitrile by the reaction shown below.

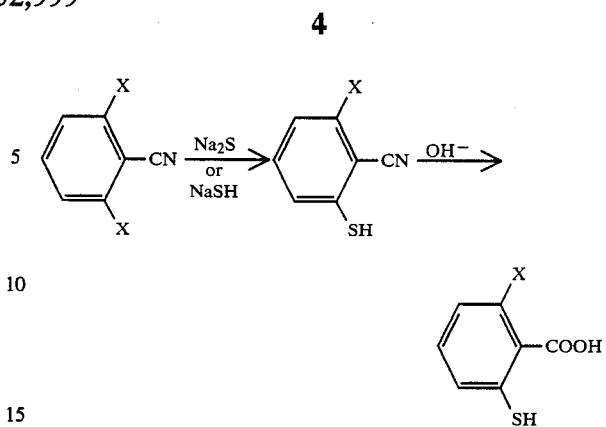

The compound of the present invention can also be prepared in accordance with the following process.

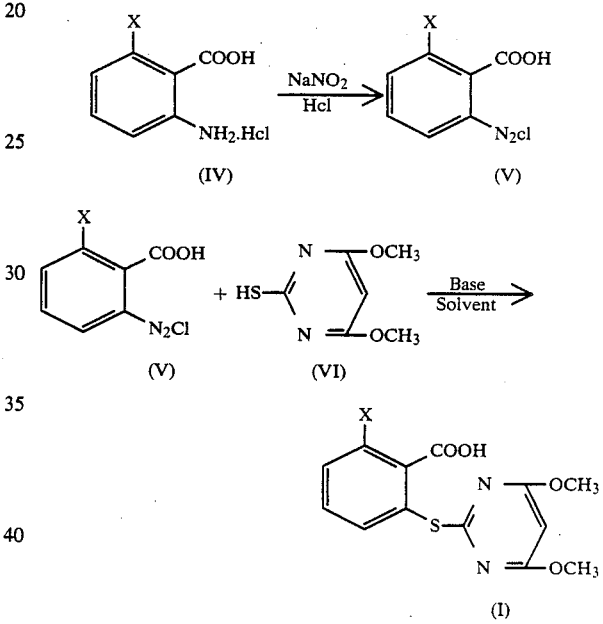

(I)

In the above formulas, X is as defined above.

The compound of the formula I can be prepared by reacting the diazonium salt of the formula V converted from the aniline derivative of the formula IV, with the compound of the formula VI in a basic solution at a low temperature, preferably within a temperature range of from −20 to 10° C.

As the diazonium salt, a hydroborate, a hydroiodate, a tetrafluoroborate or a sulfate can be used in addition to the hydrochloride. Further, the basic solution can be prepared by an addition of a strong base such as sodium hydroxide, potassium hydroxide, barium hydroxide or calcium hydroxide to a solvent.

The 2-[(4,6-dimethoxy-2-pyrimidinyl)thio]benzoic acid derivative of the formula I prepared by the above processes, may be reacted with an equivalent of sodium hydrogencarbonate, sodium hydroxide, potassium hydroxide, sodium hydride or the like to convert it to its alkali metal salt. Then, calcium chloride may be reacted to the alkali metal salt, or calcium carbonate or calcium hydride may be reacted to the corresponding benzoic acid to obtain an alkaline earth metal salt. Further, iron chloride or the like is reacted to the alkali metal salt to convert it to a transition metal salt such as an iron salt.

Now, the present invention will be described in further detail with reference to Examples. However, it should be understood that the present invention is by no means restricted to specific Examples.

EXAMPLE 1

Preparation of
2-chloro-6-[(4,6-dimethoxy-2pyrimidinyl)thio]benzoic acid (Compound No. 1) 5.0 g of 2-amino-6-chlorobenzoic acid hydrochloride was converted to a diazonium slat with 2.3 g of sodium nitride and concentrated hydrochloric acid. Then, this diazonium salt was gradually dropwise added to a solution comprising 4.8 g of 4,6-dimethoxy-2-mercaptopyrimidine, 2.4 g of sodium hydroxide and 40 ml of water at 0° C. After completion of the dropwise addition, the mixture was stirred at room temperature for 2 hours to complete the reaction. Concentrated hydrochloric acid was added to the reaction solution, and then, the mixture was extracted with ethyl acetate. The extract was dried and then the solvent was distilled off under reduced pressure. The residue thereby obtained was purified by column chromatography to obtain 1.8 g of the desired compound as ocher powder.

Melting point: 148–151° C.

EXAMPLE 2

Preparation of
2-bromo-6-[(4,6-dimethoxy-2-pyrimidinvl)thio]benzoic acid [Compound No. 10)

7.0 g of 6-bromothiosalicylic acid was dissolved in 20 ml of an aqueous solution of 4.0 g of potassium hydroxide, and then, 6.9 g of 2-methylsulfonyl-4,6-dimethoxypyrimidine and 20 ml of dimethylformamide were added thereto. The mixture was stirred at room temperature for one hour and poured into a large amount of ice water. The aqueous solution was washed with chloroform and then, neutralized with hydrochloric acid. An oily substance thereby released was extracted with diethyl ether. The diethyl ether layer was dried and passed through a FURORIDIL short column. Diethyl ether was distilled off under reduced pressure to obtain 3.9 g of the desired compound as white powder.

Melting point: 164–165° C.

EXAMPLE 3

Preparation of
2-iodo-6-[(4,6-dimethoxy-2-pyrimidinVl)thio]benzoic acid (Compound No. 11)

9.1 g of 6-iodosalicylic acid was dissolved in 20 ml of an aqueous solution of 4.3 g of potassium hydroxide, and then, 6.9 g of 2-methylsulfonyl-4,6-dimethoxypyrimidine and 20 ml of dimethylformamide were added thereto. The mixture was stirred at room temperature for one hour and poured into a large amount of ice water. The aqueous solution was washed with chloroform and then neutralized with hydrochloric acid. An oily substance thereby released was extracted with diethyl ether. The diethyl ether layer was dried and passed through a FURORIDIL short column. Diethyl ether was distilled off under reduced pressure to obtain 4.4 g of the desired compound as white powder.

Melting point: 159–163° C.

EXAMPLE 4

Preparation of triethanolammonium
2-chloro-6-[(4,6-dimethoxy-2-pyrimidinyl(thio]benzoate (Compound No. 4)

0.72 g of triethanolamine was added to 20 ml of a tetrahydrofuran solution of 1.57 g of 2-chloro-6-[(4,6-dimethoxy-2-pyrimidinyl)thio]benzoic acid, and the mixture was stirred at room temperature for 30 minutes. The solvent was distilled off under reduced pressure. The residue was crystallized by an addition of isopropyl ether to obtain 2.0 g of the desired compound as white solid.

Melting point: 94–101° C.

EXAMPLE 5

Preparation of sodium
2-chloro-6-[(4,6-dimethoxy-2-pyrimidinyl)thio]benzoate (Compound No. 5)

1.7 g of 2-chloro-6-[(4,6-dimethoxy-2-pyrimidinyl)thio]benzoic acid dissolved in 10 ml of tetrahydrofuran was gradually dropwise added to a suspension of 0.2 g of 60% sodium hydride in 20 ml of tetrahydrofuran. The mixture was reacted under stirring for 30 minutes. After completion of the reaction, the solvent was distilled off under reduced pressure. Isopropyl ether was added to the residue, and a solid was collected by filtration. The solid was dried to obtain 1.8 g of the desired compound as white powder.

Melting point: 246–250° C.

The herbicidal composition of the present invention comprises a herbicidally effective amount of the compound of the present invention and an agricultural adjuvant. The herbicide of the present invention may be used as it is or may be formulated in various formulations such as a wettable powder, a granule, an emulcifiable concentrate or a dust by blending it with a carrier, a surfactant, a dispersing agent or an adjuvant which is commonly employed for the formulation of agricultural chemicals.

As the carrier to be used for the formulation, there may be mentioned, for example, a solid carrier such as jeeklite, talc, bentonite, clay, kaolin, diatomaceous earth, white carbon, vermiculite, slaked lime, silica sand, ammonium sulfate or urea, or a liquid carrier such as isopropyl alcohol, xylene, cyclohexane or methyl naphthalene. As the surfactant and dispersing agent, there may be mentioned, for example, an alcohol-sulfuric acid ester, an alkyl aryl sulfonate, lignin sulfonate, a polyoxyethylene glycol ether, a polyoxyethylene alkyl aryl ether or a polyoxyethylene sorbitol mono-alkylate. As the adjuvant, for example, carboxymethyl cellulose, polyethylene glycol o gum arabic may be mentioned. In practical use, such a herbicide may be diluted to a suitable concentration before application, or may directly be applied.

The herbicide of the present invention may be used in combination with other herbicides.

Ther herbicide of the present invention is applied to weeds in a paddy field by irrigated soil treatment before or after the emergence of weeds or by foliage treatment. Further, the herbicide is applied to weeds in an upland field or a non-agricultural field by soil treatment before or after the emergence of weeds or by foliage treatment.

For soil treatment, the herbicide of the present invention is applied in a dose of from 1 g to 1 kg of the active ingredient per 10 ares. For foliage treatment, it is diluted to a concentration of from 1 to 10,000 ppm and applied in a dose of from 1 g to 1 kg of the active ingredient per 10 ares.

Now, Formulation Examples for the herbicidal composition of the present invention will be given. However, it should be understood that the present invention is by no means restricted to these specific Examples. In these Examples, "%" means "% by weight".

FORMULATION EXAMPLE 1 (wettable powder)

10% of Compound No. 1, 0.5% of Emulgen 810 (trademark, Kao Corporation), 0.5% of Demol N (trademark, Kao Corporation), 20% of Kunilite 201 (trademark, Kunimine Kogyo Company Ltd.) and 69% of Jeeklite CA (tradename, Jeeklite Company Ltd.) were uniformly mixed and pulverized to obtain a wettable powder.

FORMULATION EXAMPLE 2 (emulsifiable concentrate)

30% of Compound No.1, 20% of cyclohexanone, 11% of polyoxyethylene alkyl aryl ether, 4% of calcium alkylbenzenesulfonate and 35% of methyl naphthalene, were uniformly dissolved to obtain an emulsifiable concentrate.

FORMULATION EXAMPLE 3 (granule)

5% of Compound No. 1, 2% of a sodium salt of a lauryl alcohol-sulfuric acid ester, 5% of sodium lignin sulfonate, 2% of carboxymethyl cellulose and 86% of clay were uniformly mixed and pulverized. To 100 parts by weight of this mixture, 20 parts by weight of water was added, and the mixture was kneaded, and granulated into granules of from 14 to 32 mesh by means of an extrusion granulating machine, followed by drying to obtain granules.

FORMULATION EXAMPLE 4 (dust)

2% of Compound No. 2, 5% of diatomaceous earth and 93% of clay were uniformly mixed and pulverized to obtain a dust.

The compounds and the herbicidal compositions of the present invention are capable of effectively controlling annual weeds such as barnyardgrass (*Echinochloa crusgalli*), flatsedge (*Cyperus difformis*), monochoria (*Monochoria vaqinalis*), and perennial weeds such as bulrush (*Scirpus hotarui*), *Alisma canaliculatum*, *Cyperus serotinus*, *Sagittaria pygmaea* and *Eleocharis Kuroguwai*, grown in paddy fields. Further, they are capable of effectively controlling annual weeds such as barnyardgrass (*Echinochloa crus-galli*), crabgrass (*Digitaria sanguinalis*), goosegrass (*Eleusine indica*), green foxtail (*Setaria viridis*), water foxtail (*Alopecurus aegualis*), annual bluegrass (*Poa annua*), wild oat (*Avena fatua*), italian ryegrass (*Lolium multiflorum*), smartweed (*Polygonum lapathifolium*), slender amaranth (*Amaranthus viridis*), lambsquarters (*Chenopodium album*), velvetleaf (*Abutilon theophrasti*), prickly sida (*Sida spinosa*), sicklepod (*Cassia tora*), chickweed (*Stellaria media*), morningglory (*Ipomoea spp*), common cocklebur (*Xanthium strumarium*), rice flatsedge (*Cyperus iria*), broadleaf signalgrass (*Brachiaria platyphylla*), itchgrass (*Rottoboellia exaltata*), downy brome (*Bromus tectorum*), wild buckwheat (*Polygonum convolvulus*), wild mustard (*Brassica arvensis*) and devils beggartickes (*Bidens frondosa*), and perennial weeds such as purple nutsedge (*Cyperus rotundus*), johnsongrass (*Sorghum halepense*), bermudagrass (*Cynodon dactvlon*) and quackgrass (*Agropyron repens*) grown in upland fields. On the other hand, the safety to crop plants, particularly to cotton are high.

Further, the compounds of the present invention are effective to disease injuries of crop plants such as powdery mildew on cucumber and rice blast.

Now, the herbicidal activities of the herbicides of the present invention will be described with reference to Test Examples.

TEST EXAMPLE 1

(foliage treatment after the emergence of weeds in upland field)

In a pot filled with soil (surface area: 600 cm$^2$), seeds of cotton (Go), barnyardgrass (Ec), green foxtail (Se), Johnsongrass (So), smartweed (Po), slender amaranth (Am), lambsquarters (Ch) and velvetleaf (Ab) were sown, tubers of purple nutsedge (Cr) were planted and covered with soil of a thickness of from 0.5 to 1 cm. The pot was cultured in a green house at a temperature of 20 to 30° C. for 2 weeks, and then, a predetermined amount of a wettable powder prepared in accordance with Formulation Example 1 was diluted with water, and applied to the foliage at a rate of 100 liters per 10 ares. The evaluation was conducted on 14th day after the treatment. The results were evaluated in accordance with the standard as identified in Table 2, and shown by the index numbers in Table 3.

TABLE 2

| Index No. | Herbicidal effects and Phytotoxicity |
|---|---|
| 0 | No herbicidal effect (or no phytotoxicity) |
| 1 | Herbicidal effect (or phytotoxicity): more than 0% and less than 30% |
| 2 | Herbicidal effect (or phytotoxicity): at least 30% and less than 50% |
| 3 | Herbicidal effect (or phytotoxicity): at least 50% and less than 70% |
| 4 | Herbicidal effect (or phytotoxicity): at least 70% and less than 90% |
| 5 | Herbicidal effect (or phytotoxicity): more than 90% |

Comparative compounds used in Test Example 1 will be identified below (the same applies in other Tables):

Comparative Compound 1 — disclosed in U.S. Pat. No. 4,427,437

Comparative Compound 2 — disclosed in U.S. Pat. No. 4,427,437

Comparative Compound 3 — disclosed in Agr. Biol. Chem. Vol 30 9 896 (1966)

Comparative Compound 4

-continued

CF₃ group with phenyl-O-pyrimidine-Cl structure — disclosed in U.S. Pat. No. 4,427,437

Comparative Compound 5

COOH group with phenyl-S-pyrimidine(OCH₃)₂ structure — disclosed in U.S. Pat. No. 4,770,691

Comparative Compound 6

COOCH₃ group with phenyl-S-pyrimidine(OCH₃)₂ structure — disclosed in U.S. Pat. No. 4,770,691

TABLE 3

| Compound No. | Dose g/10a | Ec | Se | So | Po | Am | Ch | Ab | Cr | Go |
|---|---|---|---|---|---|---|---|---|---|---|
| 1 | 6.3 | 4 | 4 | 5 | 5 | 5 | 5 | 5 | 4 | 0 |
| 2 | 6.3 | 3 | 4 | 5 | 5 | 5 | 5 | 5 | 3 | 1 |
| 3 | 6.3 | 3 | 4 | 5 | 5 | 5 | 5 | 5 | 3 | 0 |
| 4 | 6.3 | 3 | 4 | 5 | 5 | 5 | 5 | 5 | 3 | 0 |
| 5 | 6.3 | 3 | 5 | 5 | 5 | 5 | 5 | 5 | 4 | 0 |
| 6 | 6.3 | 3 | 4 | 5 | 5 | 5 | 5 | 5 | 4 | 0 |
| 7 | 6.3 | 4 | 5 | 4 | 5 | 5 | 5 | 5 | 4 | 1 |
| 8 | 6.3 | 3 | 5 | 5 | 5 | 5 | 5 | 5 | 4 | 0 |
| 9 | 6.3 | 4 | 5 | 5 | 5 | 5 | 5 | 5 | 4 | 0 |
| 10 | 6.3 | 3 | 4 | 5 | 5 | 5 | 5 | 5 | 5 | 0 |
| 11 | 6.3 | 3 | 3 | 5 | 5 | 5 | 5 | 5 | 5 | 0 |
| Comparative Compound No. 1 | 6.3 | 0 | 0 | 0 | 0 | 0 | 0 | 0 | 0 | 0 |
| Comparative Compound No. 2 | 6.3 | 0 | 0 | 0 | 0 | 0 | 0 | 0 | 0 | 0 |
| Comparative Compound No. 3 | 6.3 | 0 | 0 | 0 | 0 | 0 | 0 | 0 | 0 | 0 |
| Comparative Compound No. 4 | 6.3 | 0 | 0 | 0 | 0 | 0 | 0 | 0 | 0 | 0 |
| Comparative Compound No. 5 | 6.3 | 0 | 0 | 0 | 0 | 0 | 0 | 0 | 0 | 0 |
| Comparative Compound No. 6 | 6.3 | 0 | 0 | 1 | 2 | 2 | 1 | 1 | 0 | 1 |

TEST EXAMPLE 2

(foliage treatment after the emergence of weeds in upland field)

In a pot filled with soild (surface area: 300 cm²), seeds of cotton (Go), morningglory (Ip) and common cocklebur.(Xa) were sown and covered with soil of a thickness of from 0.5 to 1 cm. The pot was cultured in a green house at a temperature of from 20 to 30° C. for 17 days, and then, a predetermined amount of a wettable powder prepared in accordance with Formulation Example 1 was diluted with water, and applied to the foliage at a rate of 100 liters per 10 ares. The evaluation was conducted on 15th day after the treatment. The results were evaluated in accordance with the standard as identified in Table 2, and shown by the index numbers in Table 4.

TABLE 4

| Compound No. | Dose g/10a | Phytotoxicity Go | Herbicidal effects Ip | Herbicidal effects Xa |
|---|---|---|---|---|
| 1 | 6.3 | 0 | 5 | 5 |
| 2 | 6.3 | 1 | 4 | 4 |
| 3 | 6.3 | 0 | 5 | 5 |
| 4 | 6.3 | 0 | 5 | 4 |
| 5 | 6.3 | 0 | 5 | 5 |
| 6 | 6.3 | 0 | 5 | 5 |
| 7 | 6.3 | 1 | 5 | 4 |
| 8 | 6.3 | 0 | 5 | 5 |
| 9 | 6.3 | 0 | 5 | 5 |
| 10 | 6.3 | 0 | 5 | 5 |
| 11 | 6.3 | 0 | 5 | 5 |
| 12 | 6.3 | 0 | 5 | 5 |
| 13 | 6.3 | 0 | 5 | 5 |
| 14 | 6.3 | 0 | 5 | 5 |
| 15 | 6.3 | 0 | 5 | 5 |
| Comparative Compound No. 5 | 6.3 | 0 | 0 | 0 |
| Comparative Compound No. 6 | 6.3 | 1 | 0 | 1 |

TEST EXAMPLE 3

(soil treatment before the emergence of weeds in upland field)

In a pot filled with soil (surface area: 600 cm²), seeds of cotton (Go), barnyardgrass (Ec), crabgrass (Di), Johnsonglass (So), Smartweed (Po}, slender amaranth (Am), lambsquarters (Ch) and velvetleaf (Ab) were sown, tubers or purple nutsedge (Cr) were planted and covered with soil of a thickness of from 0.5 to 1 cm. One day later from the seeding, a predetermined amount of a wettable powder prepared in accordance with Formulation Example 1 was diluted with water, and applied to the soil surface at a rate of 100 liters per 10 ares. The evaluation was conducted on 20th day after the treatment. The results were evaluated in accordance with the standard as identified in Table 2, and shown by the index numbers in Table 5.

TABLE 5

| Compound No. | Dose g/10a | Ec | Se | So | Po | Am | Ch | Ab | Cr | Go |
|---|---|---|---|---|---|---|---|---|---|---|
| 5 | 6.3 | 5 | 5 | 5 | 5 | 5 | 5 | 5 | 5 | 0 |
| 7 | 6.3 | 5 | 4 | 5 | 5 | 5 | 5 | 5 | 5 | 0 |
| 9 | 6.3 | 4 | 4 | 5 | 5 | 5 | 5 | 5 | 4 | 0 |
| 10 | 6.3 | 5 | 5 | 5 | 5 | 5 | 5 | 5 | 5 | 0 |
| 11 | 6.3 | 5 | 5 | 5 | 5 | 5 | 5 | 5 | 5 | 0 |
| Comparative Compound No. 1 | 6.3 | 0 | 0 | 0 | 0 | 0 | 0 | 0 | 0 | 0 |
| Comparative Compound No. 2 | 6.3 | 0 | 0 | 0 | 0 | 0 | 0 | 0 | 0 | 0 |
| Comparative Compound No. 3 | 6.3 | 0 | 0 | 0 | 0 | 0 | 0 | 0 | 0 | 0 |
| Comparative Compound No. 4 | 6.3 | 0 | 0 | 0 | 0 | 0 | 0 | 0 | 0 | 0 |
| Comparative Compound No. 5 | 6.3 | 0 | 0 | 0 | 1 | 0 | 0 | 0 | 0 | 0 |
| Comparative Compound No. 6 | 6.3 | 0 | 0 | 0 | 2 | 2 | 1 | 0 | 0 | 1 |

What is claimed is:

1. A pyrimidine compound having the formula:

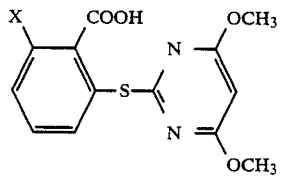 (I)

wherein X is a halogen atom, or a salt thereof.

2. The pyrimidine compound according to claim 1, wherein the halogen atom is a bromine atom, or a salt thereof.

3. The pyrimidine compound according to claim 1, wherein the halogen atom is an iodine atom, or a salt thereof.

4. The pyrimidine compound according to claim 1, wherein the salt is an alkali metal salt, an alkaline earth metal salt, a transition metal salt or an organic ammonium salt.

5. A herbicidal composition comprising a herbicidally effective amount of a pyrimidine compound of the formula I or its salt as defined in claim 1 and an agricultural adjuvant.

6. A method for killing weeds which comprises applying a herbicidally effective amount of a pyrimidine compound of the formula I or its salt as defined in claim 1 to a locus to be protected.

* * * * *